United States Patent [19]
Calanchi et al.

[11] Patent Number: 5,900,252
[45] Date of Patent: May 4, 1999

[54] METHOD FOR TARGETED AND CONTROLLED RELEASE OF DRUGS IN THE INTESTINAL TRACT AND MORE PARTICULARLY IN THE COLON

[75] Inventors: Massimo Calanchi, Monza; Marco Zema, Como; Gabriele Brunetti; Enzo Giorgetti, both of Milan, all of Italy

[73] Assignee: Eurand International S.p.A., Italy

[21] Appl. No.: 07/972,660

[22] Filed: Nov. 6, 1992

Related U.S. Application Data

[63] Continuation of application No. 07/644,062, Jan. 22, 1991, abandoned.

[30] Foreign Application Priority Data

Apr. 17, 1990 [IT] Italy ...................................... 20054/90

[51] Int. Cl.⁶ ............................... A61K 9/16; A61K 9/24; A61K 9/54
[52] U.S. Cl. ..................... 424/459; 424/451; 424/457; 424/458; 424/462; 424/464; 424/490; 424/496; 424/497
[58] Field of Search ..................................... 424/451, 463, 424/464, 474, 489, 490, 457, 458, 462, 494, 496, 497, 459

[56] References Cited

U.S. PATENT DOCUMENTS

| | | | |
|---|---|---|---|
| 4,432,966 | 2/1984 | Zeitoun et al. | 424/477 |
| 4,503,030 | 3/1985 | Edgren et al. | 424/473 |
| 4,533,562 | 8/1985 | Ikegami et al. | 427/3 |
| 4,797,287 | 1/1989 | Pich et al. | 424/464 |
| 4,800,087 | 1/1989 | Mehta | 424/497 |
| 4,808,416 | 2/1989 | Hata et al. | 424/497 |
| 4,925,676 | 5/1990 | Ghebre-Sellasie et al. | 424/470 |
| 4,983,401 | 1/1991 | Eichel et al. | 424/473 |
| 5,026,559 | 6/1991 | Eichel et al. | 424/458 |
| 5,238,686 | 8/1993 | Eichel et al. | 424/461 |

FOREIGN PATENT DOCUMENTS

| | | |
|---|---|---|
| 148811 | 7/1985 | European Pat. Off. . |
| 212745 | 3/1987 | European Pat. Off. . |
| 239361 | 9/1987 | European Pat. Off. . |
| 277925 | 8/1988 | European Pat. Off. . |
| 342522 | 11/1989 | European Pat. Off. . |
| 1147245 | 4/1969 | United Kingdom . |
| 1468172 | 3/1977 | United Kingdom . |
| 2066070 | 7/1981 | United Kingdom . |
| 2134785 | 8/1984 | United Kingdom . |
| WO85/03437 | 8/1985 | WIPO . |
| WO87/01588 | 3/1987 | WIPO . |

OTHER PUBLICATIONS

Remington's Pharmaceutical Sciences, Mack Publishing 1990, pp. 1306–1307.
Rohm Pharm–Eudragit L30 Tech. Sheet, 4 pages, Sep. 1982.

*Primary Examiner*—Robert H. Harrison

[57] ABSTRACT

The object of the present invention is to obtain a targeted and controlled release of drugs, the pharmacological action and absorption of which takes place in the intestine and in particular in the ileum and in the colon.

To achieve this objective the drug is coated with two membranes, one having pH dependent solubility and the other insoluble but permeable to intestinal juices.

As long as the coated drug remains in the stomach and in the upper part of the intestinal tract, that is as long as the pH is lower than 5.5, it is not released.

Only when it reaches an environment with a higher pH (small intestine and/or colon), the pH dependent membrane dissolves and the release of the drug can begin.

From this moment the second membrane, pH-independent but permeable to intestinal juices, carries out its action which is to slow down and control the dissolution of the drug in the small intestine-colon tract.

8 Claims, No Drawings

METHOD FOR TARGETED AND CONTROLLED RELEASE OF DRUGS IN THE INTESTINAL TRACT AND MORE PARTICULARLY IN THE COLON

This is continuation of application Ser. No. 07/644,062 filed Jan. 22, 1991 now abandoned.

DESCRIPTION

The present invention refers to a method for obtaining a targeted and controlled release of drugs which must carry out their pharmacological action in the intestine and in particular in the colon.

U.S. Pat. No. 4,503,030 refers to tablets with osmotic release, consisting of a core containing the drug, covered with a semipermeable and pH-dependent membrane in which a hole is made to put the nucleus in communication with the outside. In the stomach, the tablet remains intact and the release occurs through the hole made in the membrane, while in the intestine the membrane disintegrates completely.

U.S. Pat. No. 4,432,966 describes the preparation of tablets which disintegrate in the colon. This is achieved by coating the tablet core with two layers.

The first is made up of a pH independent polymer and microcrystalline cellulose, the second of a pH dependent polymer. The presence of microcrystalline cellulose together with the pH independent polymer, is essential to assure the disgregation of the tablet in the colon, since the microcrystalline cellulose is digested by specific enzymes and the bacteria present in the colon.

The present invention has various advantages with respect to those cited above as it relates to multidose forms instead of monodose forms.

It is known that multidose forms spread in a wide area of the gastrointestinal tract avoiding and reducing problems of irritation of the mucosa due to a high concentration of the drug, and improving absorption of same drug.

Moreover in the present invention the disintegration of the core or the membrane in the colon is not desired, but the membrane must remain intact in order to slow down the dissolution of the drug, in a time which can vary from 15 minutes to 8 hours, and consequently prolong the action along the intestine and/or the colon.

The present invention is suitable not only for drugs which act in the intestine, in particular in the colon, but also for drugs which are destroyed by gastric juices or inactivated by enzymes such as for example pancreatic and bacterial proteases of the ileum. Cited as an illustrative, but not limiting, example of these drugs are: Penicilin G, Calcitonin, Heparin, Ferritin, Sucralphate. Mebeverine Hydrochlorate, Acarbose, Dimethycone and Simethycone, immunoglobulin, anthelminthics, anti-protozoa, local and general action intestinal anti-infectants and antifungal drugs.

For some diseases of the intestine, and in particular of the colon, it is important that the drugs are transported intact to the place in which they will carry out their pharmacological action.

This is achieved by coating them with a membrane with pH-dependent solubility, and more particularly with a membrane which is soluble at a pH greater than 5.5, so that it remains intact in the stomach and first part of the intestine while it dissolves when a pH of greater than 5.5 is reached in the intestine, thus releasing the drug. But for various drugs it is also important that the contact with the mucosa, or their absorption, occurs along all the colon, and therefore it is necessary to delay the release so that the effect is prolonged in time and does not occur only in the initial tract, as happens when the drug is covered with the pH dependent membrane only.

It has now been discovered that by applying separately a membrane with pH dependent solubility and a membrane which is insoluble but permeable to intestinal fluids, the dissolution of the drug is delayed; it is released slowly and can thus carry out its action along the whole of the colon. In fact (see Example 1) if the drug is coated by a Eudragit S membrane, (which dissolves at a pH higher than 6) there is a very low release in buffered solutions up to pH 6.2 (first 3 hours), but when the pH increases to 7.2 a rapid dissolution of the drug occurs.

Only by applying a second membrane of Ethylcellulose, which is insoluble in the juices but permeable to same, on to the Eudragit membrane, is one able to delay the release of the drug and to prolong the effect for another 3 hours.

The same result is obtained if the delaying membrane (see Example 2) is applied before the pH dependent membrane, while if the two types of polymers constituting the membrane (Example 3) are mixed, the delayed effect is not obtained. Instead there is a release very similar to that obtained by applying only the pH dependent polymer.

The original characteristic of the present invention consists therefore of the consecutive application, in any order, of a membrane soluble at a given pH an insoluble but permeable membrane.

Thus a release of the drug targeted at a certain tract of the intestine (colon) and a prolonging of this release is obtained in such a way as to render it effective along the whole of the remaining intestinal tract.

DESCRIPTION OF THE PROCESS FOR COATING WITH THE FIRST MEMBRANE

The present invention is applied to multidose forms, that is drugs in the form of crystals, granules, pellets or tablets of very small dimensions, (also called minitablets) which are coated as described later. These coated drugs are then formulated in capsules, monodose sachets, in rapidly disgregating tablets or in other pharmaceutical forms suitable for oral administration.

The sizes of the single units of the multidose forms, that is of the single crystals, granules, pellets or minitablets, vary from 0.1 to 3.5 mm but must not exceed 5 mm In fact the smaller the single units are, the wider the distribution in the gastrointestinal tract, and furthermore, while the units greater than 5 mm are retained in a full stomach, units smaller than 5 mm pass through the stomach much more rapidly and in a similar way to liquids.

This phenomenon is described in the article by S. S. Davis "The Design and Evaluation of the Controlled Release Systems for the Gastrointestinal Tract" published in the "Journal of Controlled Release", 2 (1985) 27-38.

Since the drugs are often in fine powder form, these are generally granulated, using known dry or wet techniques (compacting), to obtain the desired particle size.

However it should be considered that the description which follows, that is referring to drugs in granular form is also valid for the other multidose forms, i.e. crystals, pellets and minitablets.

The granulated drug is place in UNI Glatt fluid bed container equipped with the Wurster insert and is coated, by spraying through atorniser, with a pH dependent polymer, dissolved in an organic solvent, or in a mixture of organic solvents, or in a mixture of organic solvents and water, or in solution, dispersion or aqueous emulsion.

It is also convenient to add plasticizers. Among the types of polymers constituting the pH dependent membrane the following are cited as an illustrative but not limiting example: co-polymers of Metacrylic Acid (Eudragit L, Eudragrit S), Cellulose Acetate Phthalate, Hydroxypropyl-methylcellulose Phthlate, Polyvinyl Acetate Phthalate, Shellac, Hydroxypropylmethyl-celluloseAcetate Succinate, Carboxymethylcellulose, CelluloseAcetate Trimellitate, Copolymers of Maleic Acid and Phthalic Add Derivatives.

Cited among the plasticizers are Polyethylene Glycol, Dibutyl Phthalate, Diethyl Phthalate, Citric Acid Esters and among the adjuvants: Talc, Silicon Dioxide, Titanium Dioxide, Magnesium Stearate, again as a illustrative but not limiting example.

The coated granules are dried with hot air (about 50 degrees C.) for about 30 minutes.

DESCRIPTION OF THE SECOND MEMBRANE COATING PROCESS

These granules coated with pH dependent membrane are then coated with a second pH independent membrane using analogous techniques. Also in the case one can use organic or aqueous solutions or aqueous dispersions/emulsions and it is convenient to add plasticizers and adjuvants of the above indicated type.

The following are cited among the types of polymers constituting the pH independent membrane as an illustrative but not limited example: copolymers of metacrylic esters (Eudragit RS/RL/NE), Ethylcellulose, Polyethylene, Polysiloxane, alone are mixed with each other or with other water-soluble pH independent polymers such as: Hydroxypropylmethylcellulose, Hydroxypropylcellulose, Hydroxyethycellulose, Methylcellulose, Polyvinlypyrrolidone.

The granules coated with the membrane are dried with hot air (about 50 degrees C.) for about 30 minutes.

As previously mentioned the coating with the two membranes can also be done in the opposite order to that described.

EXAMPLE 1

800 g of Mebeverine Hydrochlorate granulated with Hydroxypropylmethylcellulose and with a particle size between 710 and 1300 um was put in the UNI Glatt fluid bed container equipped with the Wurster insert.

This granulate was coated with a first membrane of Eudragit S, by spraying a suspension with the following composition with the atomiser: 468 g of Methylene Chloride, 156 g of Isopropylic Alcohol, 55.6 g of Eudragit S, 5.5 g of Dibutyl Phthalate and 28 g of Talc.

The coated granules were dried in hot air (about 50 degrees C.) for 30 minutes and then the release was determined with the USP apparatus (blade stirrer), utilizing the following sequence of artificial juices, 2 hours in 0.1N HC1, 1 hour in pH 6.2 buffer and the following hours in pH 7.2 buffer.

The following results were obtained:

| Time (hours) | 1 | 2 | 3 | 4 | 5 |
|---|---|---|---|---|---|
| Release (%) | 8 | 14 | 16 | 70 | 97 |

Then a second membrane of Ethylcellulose was applied to 700 g of these Eudragit S coated granules by spraying the following solution 199 g of Methylene Chloride, 44 g of Ethyl Alcohol, 4.3 g of Ethylcellulose, 8.6 g of Hydroxypropylmethylcellulose and 1.5 g of Diacetylated Monoglycerides and finally drying with air at 50 degrees C. for about 30 minutes. The granules coated with the two membranes were analyzed again as described above and the following results were obtained:

| Time (hours) | 1 | 2 | 3 | 4 | 5 | 6 | 8 |
|---|---|---|---|---|---|---|---|
| Release (%) | 5 | 10 | 11 | 28 | 49 | 73 | 95 |

EXAMPLE 2

700 g of Calcitonin granulated with Hydroxypropylmethylcellulose with a particle size between 710 and 1300 un was put in the UNI Glatt container equipped with Wurster insert.

These granules were coated with a first membrane of Ethylcellulose/Hydroxypropylmethylcellulose, by spraying a solution with the following composition with the atomiser: 200 g of Methylene Chloride, 45 g of Ethyl Alcohol, 6.4 g of Ethylcellulose, 6.4 g of Hydroxypropylmethylcellulose, and 1.4 g of Diacetylated Monoglycerides.

The coated granules were dried with hot air (about 50 degrees C.) for 30 minutes and then its release was determined with the USP apparatus (blade stirrer), utilizing the following sequence of artificial juices: 2 hours in HCL 0.1N, 1 hour in pH 6.2 buffer and the following hours in Ph 7.2 buffer.

The following results were obtained:

| Time (hours) | 1 | 2 | 3 | 4 | 5 |
|---|---|---|---|---|---|
| Release (%) | 27 | 51 | 69 | 83 | 99 |

Then a second Eudragit S membrane was applied to these coated granules, by spraying the following suspension: 134 g of Methylene Chloride, 65 g of Isopropyl Alcohol, 23 g of Eudragit S, 2.3 g of Dibutyl Phthalate and 11.5 of Talc and finally drying with air at 50 degrees Centigrade for about 30 minutes.

The granules coated with the two membranes were analyzed again as described above and the following results were obtained:

| Time (hours) | 1 | 2 | 3 | 4 | 5 | 6 | 8 |
|---|---|---|---|---|---|---|---|
| Release (%) | 2 | 3 | 7 | 26 | 58 | 72 | 98 |

EXAMPLE 3

800 g of Mebeverine Hydrochlorate granulated with Hydroxypropylmethylcellulose with a particle size between 710 and 1300 um was put in the UNI Glatt fluid bed container equipped with Wurster insert.

These granules were coated with a Ethylcellulose/ Hydroxypropylmethyicellulose/Eudragit S membrane, by spraying a suspension with the following composition with an atomiser: 836 g of Methylene Chloride, 418 g of Isopropyl Alcohol 5.8 g of Ethylcellulose, 11.8 g of Hydroxypropylmethylcellulose, 58.7 g of Eudragit S, 3.7 g of Dibutyl Phthalate and 29 g of Talc.

The coated granules were dried with hot air (about 45 degrees C.) for 30 minutes and then the release was determined with the USP apparatus (blade stirrer) using the following sequence of artificial juices: 2 hours in 0.1N HCl, 1 hour in pH 6.2 buffer and the following hours in pH 7.2 buffer.

The following results were obtained:

| Time (hours) | 1 | 2 | 3 | 4 | 5 | 6 |
|---|---|---|---|---|---|---|
| Release (%) | 4 | 7 | 10 | 58 | 90 | 100 |

What is claimed:

1. A targeted drug release formulation for delivery of drugs to the intestinal tract of the ileum and colon of a mammal consisting essentially of a plurality of multidose minitablet units each said unit having a particle size of less than 5 mm and consisting essentially of a minitablet core containing a drug selected from the group consisting of penicillin G, calcitronin, heparin, ferritin, sucralfate, mebeverine hydrochlorate, acarbase dimethycone, simethicone and immunoglobulin surrounded by two membranes consisting essentially of a pH dependent polymer which is soluble at a pH greater than about 5.5 and the second of said membranes consisting essentially of one or more polymers such that said membrane is substantially insoluble in but permeable to gastric fluids, and wherein
   a) said formulation is characterized with a dissolution rate in a simulated gastric environment such that over a period of 8 hours substantially all of the drug is released, and the release is further characterized by the release of no more than about 10% drug after 3 hours and no more than about 75% drug after 6 hours;
   b) said pH dependent polymer is selected from the group consisting of anionic copolymers based on methacrylic acid and methacrylic acid methyl ester, cellulose acetate phthalate, hydroxpropylmethylcellulose phthalate, polyvinyl acetate phthalate, shellac, hydroxpropylmethylcelluloseacetate succinate, carboxymethylcellulose, cellulose acetate trimellitate, copolymers of maleic acid and derivatives of phthalic acid;
   c) said substantially insoluble membrane is selected from the group consisting of copolymers formed from acrylic and methacrylic acid esters with a low content of quaternary ammonium groups, neutral copolymers based on ethyl acrylate and methyl methacrylate and having an average molecular weight of 800,000, ethylcellulose, polyethylene, polysiloxanes and mixtures thereof; and
   d) wherein the membrane containing the pH dependent polymer is interior to the other membrane.

2. The formulation of claim 1, wherein said substantially insoluble membrane further comprises a pH independent water soluble polymer selected from the group consisting of hydroxypopylmethylcellulose, hydroxypropylcellulose, hydroxyethylcellulose, methylcellulose, polyvinylpryrrolidone and mixtures therof.

3. The formulation of claim 1 further comprising a plasticizer in at lease one of the membranes.

4. The formulation of claim 2 wherein said substantially insoluble membrane is selected from the group consisting of ethyl cellulose and mixture of ethylcellulose with hydroxypropylmethylcellulose in a ratio of about 1:3 to about 3:1.

5. A pharmaceutical unit dosage form comprising the formulation of claim 1 further formulated in capsules, sachets, tablets or suspensions.

6. A method of preparing a targeted drug release of formulation for the delivery of drugs to the intestinal tract of the ileum and colon of a mammal comprising the steps of
   a) preparing a plurality of drug containing minitablet cores containing a drug selected from the group consisting of penicillin G, calcitonin, heparin, ferritin, sucralfate, mebeverine hydrochlorate, acarbase dimethylcone, simethicone and immunogloulin;
   b) coating sail cores with two separate and distinctly characterized membrane layers wherein,
      1) one said membrane layers consists essentially of a polymer which is soluble in gastric juices at a pH greater than 5.5,
      2) wherein said second polymer layer consists essentially of a polymer which is substantially insoluble in gastric juices but permeable thereto,
      3) wherein the membrane containing the pH dependent polmer is interior to the other membrane;
   c) with the proviso that said coated cores are characterized in having a dissolution rate in a simulated gastric environment such that over a period of 8 hours substantially all of the drug is released, and that release is further characterized by the release of no more than about 10% drug after 3 hours and no more than about 75% drug after 6 hours; and
   d) formulating said minitablet coated cores into unit drug dose oral delivery forms selected from the group consisting of capsules, tablets, sachets and suspension.

7. A targeted drug release formulation for delivery of drugs to the intestinal tract of the ileum and colon of a mammal consisting essentially of a plurality of multidose minitablet units each said unit having a particle size of less than 5 mm and consisting essentially of a minitablet core containing a drug selected from the group consisting of penicillin G, calcitronin, heparin, ferritin, sucralfate, mebeverine hydrochlorate, acarbase dimethycone, simethicone and immunoglobulin surrounded by two membranes consisting essentially of a pH dependent polymer which is soluble at a pH greater than about 5.5 and the second of said membranes consisting essentially of one or more polymers such that said membrane is substantially insoluble in but permeable to gastric fluids, and wherein
   a) said formulation is characterized with a dissolution rate in a simulated gastric environment such that over a period of 8 hours substantially all of the drug is released, and the release is further characterized by the, release of no more than about 10% drug after 3 hours and no more than about 75% drug after 6 hours;
   b) said pH dependent polymer is selected from the group consisting of anionic copolymers based on methacrylic acid and methacrylic acid methyl ester, cellulose acetate phthalate, hydroxpropylmethylcellulose phthalate, polyvinyl acetate phthalate, shellac, hydroxpropylmethylcelluloseacetate succinate, carboxymethylcellulose, cellulose acetate trimellitate, copolymers of maleic acid and derivatives of phthalic acid; and
   c) said substantially insoluble membrane is selected from the group consisting of copolymers formed from acrylic and methacrylic acid esters with a low content of quaternary ammonium groups, neutral copolymers based on ethyl acrylate and methyl methacrylate and having an average molecular weight of 800,000, ethylcellulose, polyethylene, polysiloxanes and mixtures thereof;

d) wherein said substantially insoluble membrane further comprises at least one pH independent water soluble polymer selected from the group consisting of hydroxypropylmethylcellulose, hydroxypropylcellulose, hydroxyethylcellulose, methylcellulose, polyvinylpryrrolidone and mixtures therof;

e) wherein the membrane containing the pH dependent polymer is exterior to the other membrane; and f) wherein at least one of the membranes comprises a plasticizer.

8. A targeted drug release formulation for delivery of drugs to the intestinal tract of the ileum and colon of a mammal consisting essentially of a plurality of multidose minitablet units each said unit having a particle size of less than 5 mm and consisting essentially of a minitablet core containing a drug selected from the group consisting of penicillin G, calcitronin, heparin, ferritin, sucralfate, mebeverine hydrochlorate, acarbase dimethycone, simethicone and immunoglobulin surrounded by two membranes consisting essentially of a pH dependent polymer which is soluble at a pH greater than about 5.5 and the second of said membranes consisting essentially of one or more polymers such that said membrane is substantially insoluble in but permeable to gastric fluids, and wherein a) said formulation is characterized with a dissolution rate in a simulated gastric environment such that over a period of 8 hours substantially all of the drug is released, and the release is further characterized by the release of no more than about 10% drug after 3 hours and no more than about 75% drug after 6 hours;

b) said pH dependent polymer is selected from the group consisting of anionic copolymers based on methacrylic acid and methacrylic acid methyl ester, cellulose acetate phthalate, hydroxpropylmethylcellulose phthalate, polyvinyl acetate phthalate, shellac, hydroxpropylmethylcelluloseacetate succinate, carboxymethylcellulose, cellulose acetate trimellitate, copolymers of maleic acid and derivatives of phthalic acid; and c) said substantially insoluble membrane is selected from the group consisting of copolymers formed from acrylic and methacrylic acid esters with a low content of quaternary ammonium groups, neutral copolymers based on ethyl acrylate and methyl methacrylate and having an average molecular weight of 800,000, ethylcellulose, polyethylene, polysiloxanes and mixtures thereof;

d) wherein the membrane containing the pH dependent polymer is exterior to the other membrane; and e) wherein at least one of the membranes comprises a plasticizer.

* * * * *